United States Patent [19]
Zeluff

[11] Patent Number: 4,606,336
[45] Date of Patent: Aug. 19, 1986

[54] METHOD AND APPARATUS FOR NON-SURGICALLY STERILIZING FEMALE REPRODUCTIVE ORGANS

[76] Inventor: James W. Zeluff, 1010 E. McDowell Rd., Suite 300, Phoeniz, Ariz. 85006

[21] Appl. No.: 674,244

[22] Filed: Nov. 23, 1984

[51] Int. Cl.⁴ .................. A61F 5/46; A61M 31/00
[52] U.S. Cl. .................. 128/130; 128/82.1; 128/127; 604/55
[58] Field of Search .................. 604/55; 128/127, 130, 128/82.1

[56] References Cited

U.S. PATENT DOCUMENTS

| Re. 29,345 | 4/1974 | Erb | 128/1 |
|---|---|---|---|
| 3,680,542 | 8/1972 | Cimber | 128/1 |
| 3,909,852 | 10/1975 | Homsy | 128/92 |
| 3,918,431 | 11/1975 | Sinnreich | 128/130 |
| 4,052,754 | 10/1977 | Homsy | 128/82.1 |
| 4,135,495 | 1/1979 | Borgen | 126/1 |
| 4,509,504 | 4/1985 | Brundin | 128/130 |

OTHER PUBLICATIONS

"Female Transcervical Sterilization", Gerald I. Zatuchni, et al., Harper & Row 1983, pp. 7–23, 234–239, 240–244.
"Advances in Female Sterilization Techniques", John J. Sciarra, et al, Harper & Row, 1976, pp. 169–175, 182–196, 259–271.
"Clinical Application of Hysteroscopic Sterilization Using Uterotubal Junction Blocking Devices" by Abdol H. Hosseinian and Wilson A. Morales.
"Hysteroscopic Implantation of Uterotubal Junction Blocking Devices" by Abdol H. Hosseinian, Sollie Lucero and Moon H. Kim, MD.
"A Steerable Hysteroscope and Mechanical Tubal Occlusive Devices" by Erich E. Breuschke, MD; Lourens J. D. Zaneveld, DVM, PhD; George D. Wilbanks, MD; Julian T. Archie, MD and Eugene F. Uretz, MD.
"Anatomic and Physiological Factors Affecting the Development of Trancervical Sterilization Techniques" by Carlton Eddy and Carl J. Pauerstein.
"Hydrogel Tubal Blocking Device P-Block" by Jan Brudin.
"Silastic: A Retrievable Custom-Molded Oviductal Plug" by Robert A. Erb, Ph.D.

Primary Examiner—Herbert S. Cockeram
Attorney, Agent, or Firm—Cahill, Sutton & Thomas

[57] ABSTRACT

An ostial occlusion device forms an hermetic seal around the tubal ostium of the uterotubal junction and includes a hub fabricated from a non-porous material having a circumferential edge and upper and lower surfaces. A locator pin is oriented perpendicular to and extends outward from the lower surface of the hub and is insertable into the fallopian tube at the uterotubal junction to center the hub about the tubal ostium. A ring of porous material surrounds the circumferential edge of the hub and includes an exposed lower surface which contacts the tissue surrounding the tubal ostium and receives fibroblast ingrowth to create an hermetic seal around the tubal ostium. This hermetic seal isolates the fallopian tube from the uterine cavity and renders the female reproductive system infertile.

31 Claims, 13 Drawing Figures

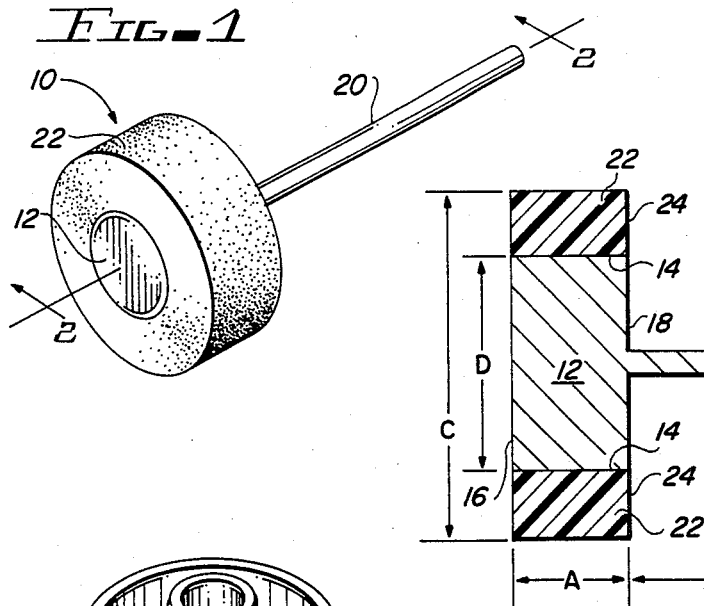
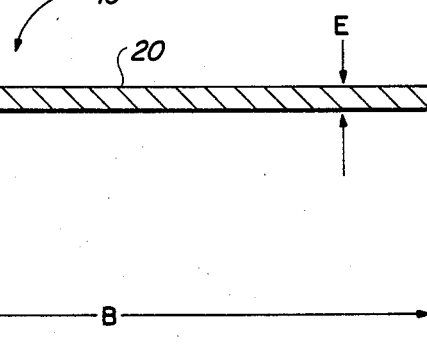
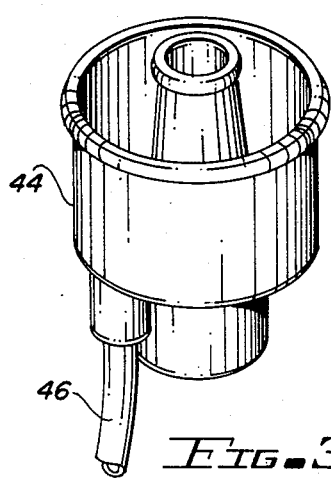
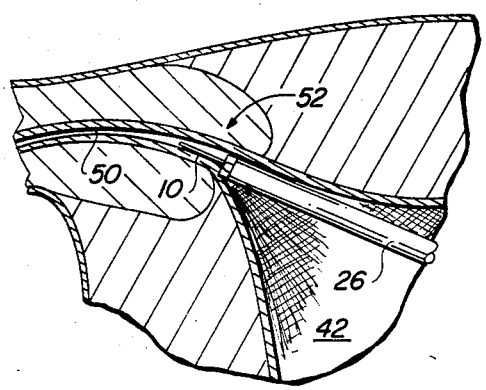
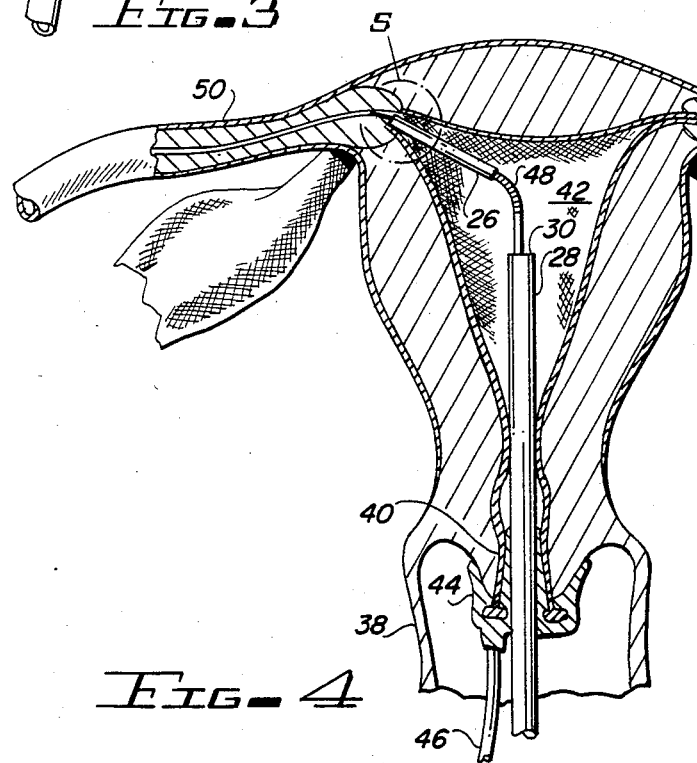
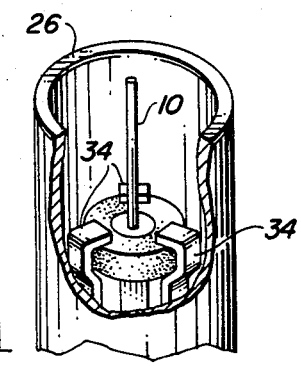

METHOD AND APPARATUS FOR NON-SURGICALLY STERILIZING FEMALE REPRODUCTIVE ORGANS

BACKGROUND OF THE INVENTION

1. Field of the Invention

This invention relates to female sterilization methods and apparatus, and more particularly, to female sterilization methods and apparatus which operate by blocking the discharge of ova from the fallopian tubes into the uterine cavity.

2. Description of the Prior Art

A wide variety of techniques and apparatus have been developed in the past for either permanently or reversibly sterilizing the female reproductive organs. In U.S. Pat. No. Re. 29,345 (Erb) discloses a method and apparatus for ejecting a curable elastomeric composition through an aperture in a tip coupled to the end of an insertion device to form a plug within the fallopian tube. Although the tip adheres to the resulting elastomeric oviduct block, neither the tip nor the elastomeric material adheres to the tissue of the uterus or fallopian tube. The Erb plug injection system requires careful mixing and application of the elastomeric sealant and consumes a significant amount of time to accomplish the entire procedure, including the time during which the elastomeric material cures. Creation of the type of plug disclosed by Erb produces an elongated barrier which restricts and essentially eliminates the passage of both eggs and sperm through the fallopian tube. In a subsequent article entitled "Hysteroscope Oviductal Blocking With Formed-In-Place Silicone Rubber Plugs," Erb updates his prior fluoroscopic technique as disclosed in his patent by adopting a hysteroscopic procedure which permits optically monitored placement of the tip at the uterotubal junction area. At page 67, second column of this article, Erb confirms that his elastomeric plug does not adhere to the tissues of the female reproductive organs and may be withdrawn in one piece. In his last sentence at page 67 of his article, Erb indicates that his plugs are larger in diameter at both ends and narrower in the middle, a configuration important to retention of his oviduct blocking plugs.

In U.S. Pat. No. 4,135,495, Borgen discloses a method and apparatus for reversibly sterilizing the female reproductive organs. Borgen's invention involves abdominal surgery in which a cap is placed over and sutured to the fimbriated ends of the fallopian tubes. The caps prevent union of sperm and ova and prevent pregnancy. Subsequent abdominal surgery permits access to the caps which can be removed from the ends of the fallopian tubes without damage to the reproductive organs.

In U.S. Pat. No. 3,680,542, Cimber discloses an oviduct blocking device which is positioned during the course of abdominal surgery by inserting the device through the open end of the fallopian tube adjacent to the overy. Cimber's pointed guide member is removed through a surgical incision in the wall of the fallopian tube. If desired, subsequent abdominal surgery can be performed to remove the oviduct blocking plug to thereby reverse the sterilization procedure previously accomplished.

In an article entitled "Clinical Application of Hysteroscopic Sterilization Using Uterotubal Junction Blocking Devices," Hosseinian and Morales disclose the use of conical plastic plugs including bar-like retention devices as illustrated in FIG. 30-1 at page 235. In FIG. 30-2 at page 237, the authors disclose the proper method of inserting their plug into the uterotubal junction and retaining the plug in place by causing the plug-mounted barbs to penetrate into the tissue adjacent to the uterotubal junction. Hysteroscopic techniques were used to insert and remove the plug. At page 235, the device carrier is disclosed as being fabricated from stainless steel and including a tip with three grasping teeth, a shaft and a handle.

In an article entitled "Hysteroscopic Implantation of Uterotubal Junction Blocking Devices," Hosseinian, Lucero and Kim disclose uterotubal blocking plugs of a design substantially similar to that discussed in the article by Hosseinian described above. Further details of the device carrier are illustrated in FIGS. 3 and 4 at page 172.

In an article entitled "A Steerable Hysteroscope and Mechanical Tubal Occlusive Devices," Brueschke, Zaneveld, Wilbanks, Archie and Uretz disclose uterotubal plugging devices of the type illustrated in FIG. 6 at page 189. The disclosed conical plugs include metallic retention anchors or barbs "A" with a medical grade silicone rubber body "B" having a threaded retention member for securing the plug to a delivery wire.

In an article entitled "Anatomic and Physiological Factors Affecting the Development of Transcervical Sterilization Techniques," Eddy and Pauerstein in FIG. 2-8 at page 18 disclose the use of a Silastic sphere lodged in the lumin to occlude the lumin and prevent pregnancy.

In an article entitled "Hydrogel Tubal Blocking Device: P-Block," Burndin discloses an oviductal blocking device having a hydrogel body and two millimeter wide nylon wings which prevent expulsion from the fallopian tube before hydratization of the blocking device and subsequent water retention induced swelling. FIG. 31-1 at page 241 depicts the hydrogelic tubal blocking devices disclosed in the article.

In U.S. Pat. No. 3,909,852, Homsy discloses an implantable substitute structure for the middle ear bony chain. A rigid strut 12 maintains a fixed spacing between ends 14 and 16 which are fabricated from growth promoting porous material such as carbon bonded by PTFE plastic. The interior surfaces of pads 14 and 16 are covered with pore closing means for the express purpose of preventing tissue growth in this area which might adversely effect the sound transmitting qualities of the device. Such pore closing means is discussed in detail at column 2, lines 33-46 of the Homsy patent.

DESCRIPTION OF THE DRAWINGS

The invention is pointed out with particularity in the appended claims. However, other objects and advantages together with the operation of the invention may be better understood by reference to the following detailed description taken in conjunction with the following illustrations, wherein:

FIG. 1 is a perspective view of the ostial occlusion device of the present invention.

FIG. 2 is a sectional view of the ostial occlusion device depicted in FIG. 1, taken along section line 2—2.

FIG. 3 is a perspective view of a suction device which may be used to stabilize the operating hysteroscope during insertion of the ostial occlusion device.

FIG. 4 is a partially cutaway view of the female reproductive organs indicating the manner in which the ostial occlusion device of the present invention is inserted.

FIG. 5 is an enlarged sectional view of the area depicted in FIG. 4 further illustrating, the positioning of the ostial occlusion device in the female reproductive organs.

FIGS. 6A and 6B depict the carrier device which houses and ejects the ostial occlusion device.

SUMMARY OF THE INVENTION

Figure 6B:
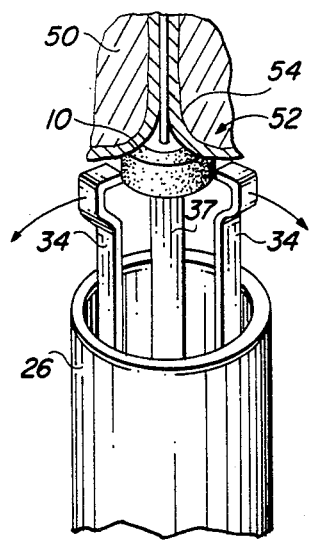

It is therefore a primary object of the present invention to provide an ostial occlusion device which creates an hermetic seal at the uterotubal junction by promoting ingrowth of fibroblasts into a ring of porous material forming a part of the ostial occlusion device.

Another object of the present invention is to provide an ostial occlusion device having a lower central surface fabricated from a non-porous material for preventing fibroblast ingrowth between that non-porous surface and the tubal ostium section of the uterotubal junction.

Yet another object of the present invention is to provide an ostial occlusion device which forms an unpressurized seal across the uterotubal junction without creating a cork-like compressive force between the inner surface of the fallopian tube and a blocking plug.

Still another object of the present invention is to provide an ostial occlusion device which is maintained in position by naturally occurring fibroblast ingrowth rather than by reliance on mechanical barbs penetrating into the surface of the female reproductive organs.

Still another object of the present invention is to provide an ostial occlusion device which can be inserted into and readily removed from the female reproductive organs without abdominal surgery and without damage to those organs.

Still another object of the present invention is to provide an ostial occlusion device which can be inserted into and removed from the female reproductive organs by a vaginally inserted operative hysteroscope.

Still another object of the present invention is to provide an ostial occlusion device which can reversibly sterilize the female reproductive organs.

Briefly stated, and in accord with one embodiment of the invention, an ostial occlusion device forms an hermetic seal around the tubal ostium area of the female reproductive system. The device includes a hub fabricated from a non-porous material and includes a circumferential edge and upper and lower surfaces. A locator pin is oriented perpendicular to and extends outward from the lower surface of the hub and is insertable into the end of the fallopian tube at the uterotubal junction of the female reproductive organs to center the hub about the tubal ostium. A ring of porous material surrounds the circumferential edge of the hub and includes an exposed lower surface for contacting the tissue surrounding the tubal ostium and for receiving fibroblast ingrowth to create an hermetic seal surrounding the tubal ostium to provide fluid isolation between the fallopian tube and the uterine cavity to thereby render the female reproductive system infertile. The present invention also includes a method for forming the hermetic seal at the uterotutal junction by introducing the ostial occlusion device described above into the uterine cavity through the vagina and cervix, by then inserting the locator pin of the ostial occlusion device into the uterotubal junction until the exposed lower surface of the ring of porous material contacts the tissue surrounding the uterotubal junction, and by then maintaining the lower surface of the ring of porous material in contact with the tissue surrounding the uterotubal junction until fibroblast ingrowth into the porous material commences.

DESCRIPTION OF THE PREFERRED EMBODIMENT

In order to better illustrate the advantages of the invention and its contributions to the art, a preferred hardware embodiment of the invention will now be described in detail.

Referring now to FIGS. 1 and 2, the ostial occlusion device 10 of the present invention includes a hub 12 fabricated from a rigid, non-porous material such as steel or radiopaque plastic. Hub 12 includes a circumferential edge 14, an upper surface 16 and a lower surface 18. Centering means in the form of a locator pin 20 is oriented perpendicular to and extends outward from lower surface 18 of hub 12. Locator pin 20 and hub 12 may either be fabricated as a single unit or may be separately fabricated and coupled together by a tack weld, an adhesive bond or by other well known techniques.

A ring of porous material 22 surrounds the circumferential edge 14 of hub 12 and includes an exposed lower surface 14. Ring 22 may be fabricated from porous expanded materials such as polytetrafluoroethylene (PTFE) plastic which is a well known existing material sold under the trademark TEFLON. Appropriate porous PTFE materials are commercially available and may be produced by the process described in Japanese Patent Publication No. 135,60/67 and U.S. Pat. No. 3,953,566, the disclosures of which are hereby incorporated by reference. Other acceptable porous materials are manufactured and sold under the trademarks PROPLAST or GORTEX.

The ring of porous material 22 includes micro porous fibrous structure consisting of small fibers and nodes connected together. Similar expanded PTFE products are presently in use for vascular prostheses and typically include pore sizes on the order of two microns or greater. Typical pore size for most effective utilization in vascular prostheses generall fall within the range of between approximately five to ten microns.

The dimension lines depicted in FIG. 2 in combination with the measurements incorporated in Table 1 below designate one specific configuration of a preferred embodiment of the ostial occlusion device of the present invention:

TABLE 1

| | |
|---|---|
| A | 1.00 mm |
| B | 5.00 mm |
| C | 2.95 mm |
| D | 1.45 mm |
| E | 0.25 mm |

Referring now to FIGS. 3–6, the method for using the ostial occlusion device of the present invention to sterilize female reproductive organs will be described in some detail.

Figure 7:
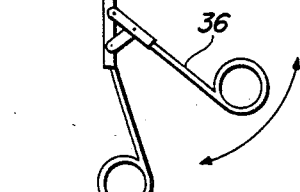
FIG. 7 is an elevational view of the carrier control device which extends through the hysteroscope and houses the ostial occlusion device.

As depicted in FIG. 5A, ostial occlusion device 26 is housed within a carrier 26 which is longitudinally displaceable within the operating channel of a hysteroscope 28 as depicted in FIG. 4. A hysteroscope is a commercially available device used primarily by gynecologists for examining and operating on the female reproductive organs. Hysteroscope 28 typically includes three parallel oriented channels which run longitudinally along the typical two foot length of the device. One of these channels provides a source of illumination emanating from the end 30 of hysteroscope 28. A second channel includes a fiberoptic bundle retransmitting light rays received from an area in proximity to the end of hysteroscope 28 to the eye of the observer/physician. The third channel of typically three millimeters in diameter and serves an operating channel for housing carrier 28 and the carrier control device 32 as illustrated in FIGS. 4 and 7.

As depicted by FIG. 6A, ostial occlusion device 10 is maintained in carrier 26 by a plurality of three spaced apart arms or clamps 34. Displacement of the finger-actuated lever 36 linearly displaces shaft 37 and ejects ostial occlusion device 10 from carrier 26 while simultaneously releasing clamps 34 as depicted in FIGS. 6B and 7.

As illustrated in FIG. 4, hysteroscope 28 is inserted into the uterine cavity 42 through vagina 38 and cervix 40. A suction cup 44 and suction hose 46 may be coupled to the mouth of cervix 40 prior to the insertion of hysteroscope 28 if desired to serve as a guide.

After the hysteroscope 28 has been inserted into the uterine cavity as depicted in FIG. 4, carrier control device 32 is displaced linearly along the length of the hysteroscope to eject carrier 26 from the hysteroscope. The shaft of carrier control device 32 includes a spring 48 which is manufactured with a preformed deflection on the order of approximately thirty-seven degrees so that extension of carrier control device 32 as depicted in FIG. 4 causes spring 48 to deflect the carrier 26 at the appropriate angle to permit housing 26 to be readily aligned with the uterotubal junction target.

Figure 8:
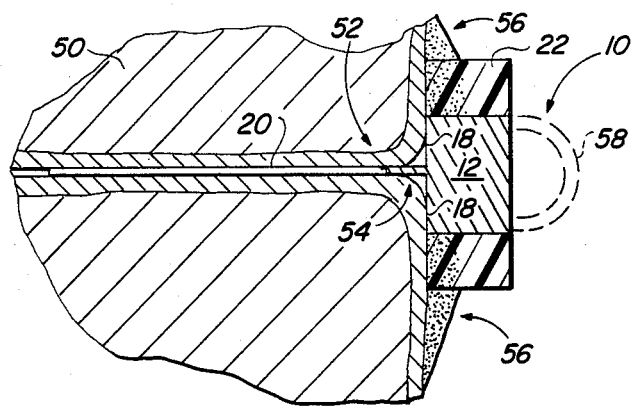
FIG. 8 is a sectional view indicating the manner in which the ostial occlusion device becomes sealed to the uterotubal junction area of the female reproductive organs.
Figure 9:
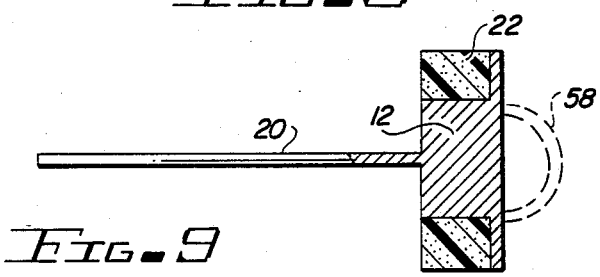
FIG. 9 is a sectional view of a second embodiment of the ostial occlusion device.
Figure 10:
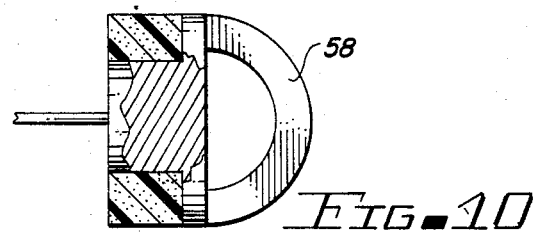
FIG. 10 is a partially cutaway section view of another embodiment of the ostial occlusion device.
Figure 11:
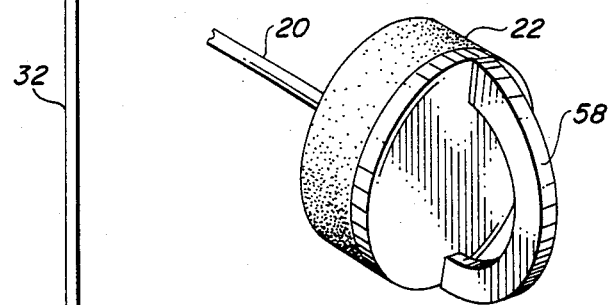
FIG. 11 is a partially cutaway perspective view of the ostial occlusion device depicted in FIG. 10.

Referring now to FIGS. 4, 5 and 8, the end of carrier 26 is aligned with the junction between the uterine cavity 42 and the fallopian tube 50. This area is commonly referred to as the uterotubal junction and has been designated by reference number 52.

After the uterotubal junction 52 has been visually identified, the end of carrier 26 is aligned with that junction and positioned in contact with it. Finger-actuated levers 36 are then actuated to eject ostial occlusion device 10 into the uterotubal junction as depicted in FIGS. 5 and 6B. Locator pin 20 assists in maintaining the desired alignment between hub 12 and uterotubal junction 52.

As carrier ejection shaft 37 maintains the lower surface 24 of ring 22 in contact with the tissue surrounding the tubal ostium 54, fibroblast ingrowth between that surrounding tissue and the porous adjacent surface of ring 22 commences immediately to form an initially weak but progressively stronger bond between ostial occlusion device 10 and the uterotubal junction tissue. A very light coat of an adhesive may be applied to the exterior surface of locator pin 20 or to the lower surface of ring 24 to initially maintain the required contact between the ostial occlusion device 10 and the underlying adjacent tissue so that the exposed porous lower surface 24 of ring 22 can accept immediate fibroblast ingrowth. In an election is made not to use an adhesive, ostial occlusion device 10 should be gently biased against the surface of the uterotubal junction 52 for a time sufficiently long to permit a degree of fibroblast ingrowth sufficient to initially secure the ostial occlusion device 10 to the adjacent tissue.

Figure 12:
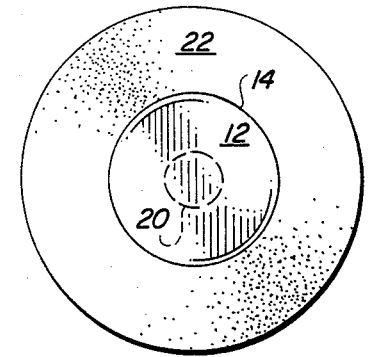
FIG. 12 is a sectional view of the ostial occlusion device depicted in FIG. 8 indicating the area over which the hermetic seal between the ostial occlusion device and the uterotubal junction area is formed.

As illustrated in FIG. 8, after a period of time, a complete hermetic seal is formed between ring 22 and the tissue surrounding the uterotubal junction area 42 as a result of the fibroblast ingrowth between these two areas. In FIG. 8, such fibroblast ingrowth is indicated by reference number 56. The presence of the non-porous material on the lower surface 18 of hub 12 prevents fibroblast ingrowth between this part of ostial occlusion device 10 and the tissue 59 immediately adjacent to the tubal ostium as illustrated in FIG. 8, which is important to the reversibility of the sterilization achieved by the present invention. FIG. 12 represents a cross sectional view of the FIG. 8 illustration taken along a line nearly adjacent to the lower surface of the ostial occlusion device 10. The shaded area within porous ring 22 represents fibroblast ingrowth. Until a complete hermetic seal has been created between the ostial occlusion device and the uterotubal junction, a patient-user should continue to rely on conventional contraceptive techniques.

Referring now to FIGS. 8–11, ostial occlusion device removal means in the form of an eyelet 58 may be provided to facilitate reversibility of the sterilization device and method described above. In such an embodiment of the ostial occlusion device, the hermetic seal created between porous ring 22 and the uterotubal junction 52 can be destroyed by the application of direct traction by a gripping tool positioned for example within carrier 26 of hysteroscope 28. Gentle curretage or heat generated by a laser light beam could be used to weaken or destroy the hermetic seal created by fibroblast bonding prior to the application of direct traction to the ostial occlusion device. Because of the comparatively strong mechanical bonding which will exist between porous ring 22 and the tissue of the uterotubal junction, some of the porous material may be left behind following removal of the ostial occlusion device 10. This should not present serious difficulties or complications for at least two reasons. First, any remaining porous material will be radially displaced away from the tubal ostium and will not interfere with the passage of either ova or sperm through the fallopian tube. Second, PTFE plastic materials have not been demonstrated to be carcinogenic and should not produce any long term adverse effects on the adjacent tissue.

The relative ease or difficulty of removing the ostial occlusion device from the uterotubal junction area can be modified by varying the porosity size of porous material 22. The utilization of a porous material having a smaller average pore size reduces the degree of fibroblast bonding and facilitates the removal of the ostial occlusion device. In certain applications, it may be desirable to maximize the bond between the ostial occlusion device and the uterotubal junction area by using a ring 22 having larger average pore diameter to maximize the fibroblast bonding between porous material and the adjacent tissue.

The ostial occlusion device is typically manufactured from either stainless steel or from a radiopaque plastic material so that if necessary a radiological examination can determine whether the ostial occlusion devices are still present at both uterotubal junctions.

It will be apparent to those skilled in the art that the method and apparatus for reversibly and non-surgically sterilizing female reproductive organs may be modified in numerous ways and may assume various embodiments other than the preferred embodiments specifically set out and described above. Accordingly, it is intended by the appended claims to cover all such modifications of the invention which fall within the true spirit and scope of the invention.

I claim:

1. An ostial occlusion device for forming an hermetic seal around the tubal ostium of the female reproductive system comprising:
   a. a hub fabricated from a rigid, non-porous material including a circumferential edge and an upper surface and a lower surface;
   b. means fabricated from a rigid, non-porous material oriented perpendicular to and extending outward from the lower surface of the hub insertable into the uterotubal junction of the female reproductive system for centering the nub about the tubal ostium; and
   c. a ring of porous material surrounding the circumferential edge of the hub and including an exposed lower surface for contacting the tissue surrounding but not including the tubal ostium and for receiving fibroblast ingrowth to create an hermetic seal surrounding but not including the tubal ostium to provide fluid isolation between the fallopian tube and the uterine cavity to thereby render the female reproductive system infertile,
whereby the non-porous lower surface of the hub extends radially outward from the hub centering means over the tissue immediately adjacent to the tubal ostium to prevent fibroblast ingrowth into said tissue.

2. The ostial occlusion device of claim 1 wherein the hub is fabricated from a rigid material and includes a cylindrical body having a constant radius, smooth circumferential edge.

3. The ostial occlusion device of claim 2 wherein the hub centering means includes a locator pin coupled to the center of the lower surface of the hub.

4. The ostial occlusion device of claim 3 wherein the length of the locator pin is equal to or greater than twice the hub diameter.

5. The ostial occlusion device of claim 1 wherein the ring of porous material is formed from a biocompatible material which stimulates ingrowth of fibroblastic tissue.

6. The ostial occlusion device of claim 1 wherein the porous material includes pores exceeding one micron in size.

7. The ostial occlusion device of claim 6 wherein the porous material includes pores having a size less than twenty microns.

8. The ostial occlusion device of claim 1 further including removal means for permitting a tool to grip ostial occlusion the device and remove it from the female reproductive system.

9. The ostial occlusion device of claim 8 wherein said removal means includes an eyelet coupled to the hub.

10. The ostial occlusion device of claim 9 wherein the eyelet is coupled to the upper surface of the hub.

11. The ostial occlusion device of claim 1 wherein the exposed lower surface of the ring of porous material is aligned with the lower surface of the hub.

12. The ostial occlusion device of claim 1 wherein the hub and the hub centering means are fabricated from radiopaque material.

13. The ostial occlusion device of claim 3 wherein the locator pin is formed as a cylinder having a smooth outer surface freely insertable into and removable from the fallopian tube.

14. The ostial occlusion device of claim 13 wherein the locator pin includes a blunt tip.

15. The ostial occlusion device of claim 13 wherein the upper and lower surfaces of the ring of porous material are aligned with the upper and lower surfaces of the hub and wherein the ring of porous material is formed as a torus surrounding and firmly contacting the circumferential edge of the hub.

16. The ostial occlusion device of claim 15 wherein the outer diameter of the ring of porous material is equal to or less than three millimeters.

17. The ostial occlusion device of claim 1 further comprising a layer of adhesive applied to the ring of porous material to initially secure the porous material to the tissue surrounding the tubal ostium to thereby maintain a fixed spatial relationship between the ostial occlusion device and the female reproductive system as fibroblast ingrowth commences.

18. The ostial occlusion device of claim 1 further comprising a layer of adhesive applied to the ring to initially secure the porous material to the tissue surrounding the tubal ostium to thereby maintain a fixed spatial relationship between the ostial occlusion device and the female reproductive system as fibroblast ingrowth commences.

19. A method for forming an hermetic seal at the junction between the fallopian tube and the uterine cavity of the female reproductive system to render a female infertile, comprising the steps of:
   a. introducing an ostial occlusion device through the vagina and cervix into the uterine cavity, the ostial occlusion device including (1) a hub having a circumferential edge and upper and lower surfaces; (2) hub centering means extending outward from the lower surface of the hub; and (3) a ring of porous material surrounding the circumferential edge of the hub and including an exposed lower surface;
   b. inserting the hub centering means of the ostial occlusion device into the uterotubal junction until the exposed lower surface of the ring of porous material contacts the tissue surrounding the tubal ostium area of the uterotubal junction; and
   c. maintaining the lower surface of the ring of porous material in contact with the tissue surrounding the uterotubal junction until fibroblast ingrowth into the porous material commences.

20. The method of claim 19 including the further step of visually identifying the uterotubal junction prior to inserting the ostial occlusion device into the uterotubal junction.

21. The method of claim 19 wherein the step of introducing the ostial occlusion device is accomplished by an hysteroscope.

22. The method of claim 21 wherein the ostial occlusion device is housed within a carrier within the hysteroscope.

23. The method of claim 19 wherein the hub is fabricated from a rigid, non-porous material for preventing fibroblast ingrowth between the tubal ostium area of the uterotubal junction and the lower surface of the hub.

24. The method of claim 19 including the further step of increasing the degree of fibroblast ingrowth between the porous material and the adjacent tissue surrounding the uterotubal junction to complete the formation of an hermetic seal between the fallopian tube and the uterine cavity of the female reproductive system.

25. The method of claim 24 wherein the hub centering means further includes removal means for permitting a tool to grip the ostial occlusion device and remove it from the female reproductive system and including the further step of using the tool to remove the ostial occlusion device from the uterotubal junction to destroy the hermetic seal between the fallopian tube and the uterine cavity to reopen the uterotubal junction.

26. The method of claim 23 wherein the ring of porous material is formed from a biocompatible material which stimulates ingrowth of fibroblast tissue.

27. The method of claim 19 further comprising a layer of adhesive applied to the ostial occlusion device for temporarily maintaining the lower surface of the ring of porous material in contact with the tissue surrounding the uterotubal junction until the ingrowth of fibroblast material has advanced to a predetermined level.

28. The method of claim 27 wherein the layer of adhesive is applied to the ring of porous material.

29. The method of claim 27 wherein the layer of adhesive is applied to the hub centering means.

30. The method of claim 22 including the further step of displacing the carrier from the hysteroscope and aligning the carrier with the uterotubal junction prior to inserting the ostial occlusion device into the uterotubal junction.

31. The method of claim 19 wherein the hub centering means includes a locator pin coupled to the center of the lower surface of the hub.

* * * * *